(12) United States Patent  
Zhou et al.

(10) Patent No.: US 7,115,231 B1
(45) Date of Patent: Oct. 3, 2006

(54) PARALLEL REACTOR WITH KNIFE-EDGE SEAL

(75) Inventors: Xiao Ping Zhou, Lompoc, CA (US); Sam Bergh, San Francisco, CA (US); Christopher E. Dube, Lexington, MA (US); Lynn Van Erden, Livermore, CA (US)

(73) Assignee: Symyx Technologies, Inc., Santa Clara, CA (US)

( * ) Notice: Subject to any disclaimer, the term of this patent is extended or adjusted under 35 U.S.C. 154(b) by 0 days.

(21) Appl. No.: 09/691,421

(22) Filed: Oct. 17, 2000

Related U.S. Application Data (60) Continuation-in-part of application No. 09/607,535, filed on Jun. 29, 2000, now Pat. No. 6,869,799, which is a division of application No. 09/093,870, filed on Jun. 9, 1998, now Pat. No. 6,149,882.

(51) Int. Cl.
*B01L 3/00* (2006.01)

(52) U.S. Cl. .................................. 422/102

(58) Field of Classification Search ............. 422/102, 422/104, 129–131, 134, 99, 101, 103; 436/124, 436/180; 435/233.4; 220/285.4, 258.4
See application file for complete search history.

(56) References Cited

U.S. PATENT DOCUMENTS

| | | | | |
|---|---|---|---|---|
| 2,771,399 A | * | 11/1956 | Savage | 435/33 |
| 3,432,275 A | * | 3/1969 | Unger | 422/102 |
| 4,014,657 A | | 3/1977 | Gryaznov et al. | 23/288 |
| 4,040,234 A | * | 8/1977 | Stockdale et al. | 53/471 |
| 4,154,795 A | | 5/1979 | Thorne | 422/99 |
| 4,545,958 A | | 10/1985 | Dopatka | 422/102 |
| 4,599,314 A | | 7/1986 | Shami | 435/287 |
| 4,599,315 A | | 7/1986 | Terasaki et al. | 435/301 |
| 4,659,222 A | | 4/1987 | Ekholm | 356/244 |
| 4,719,087 A | | 1/1988 | Hanaway | 422/102 |
| 4,721,679 A | | 1/1988 | Yiu et al. | 435/301 |
| 4,747,693 A | | 5/1988 | Kahl | 366/208 |
| 4,786,601 A | | 11/1988 | Rothenberg | 435/301 |
| 4,895,706 A | | 1/1990 | Root et al. | 422/102 |
| 4,948,442 A | * | 8/1990 | Manns | 156/73.1 |
| 4,963,493 A | | 10/1990 | Daftsios | 435/287 |
| 5,011,779 A | | 4/1991 | Maimon | 435/293 |
| 5,035,866 A | | 7/1991 | Wannlund | 422/102 |
| 5,048,957 A | | 9/1991 | Berthold et al. | 356/246 |
| 5,056,427 A | | 10/1991 | Sakabe et al. | 100/211 |
| 5,110,556 A | | 5/1992 | Lyman et al. | 422/101 |

(Continued)

FOREIGN PATENT DOCUMENTS

DE 41 14 611 A1 11/1991

(Continued)

OTHER PUBLICATIONS

Product Brochure "Calypso System Valve Base Reaction Frame"; Charybdis Technologies, Inc.

(Continued)

*Primary Examiner*—Jeffrey R. Snay (57) ABSTRACT

An apparatus for use in parallel reaction of materials. The apparatus includes a base having a plurality of reaction wells formed therein and a sealing device positioned over the reaction wells for individually sealing each of the reaction wells. One of the sealing device and the base having chamfered ridges extending generally around a periphery of each of said plurality of reaction wells. The other of the sealing device and the base having a contact surface formed of a material softer than the material of the chamfered ridges to create a knife-edge seal between the sealing device and the base when the sealing device and the base are forced into contact with one another.

22 Claims, 5 Drawing Sheets

U.S. PATENT DOCUMENTS

| | | | |
|---|---|---|---|
| RE34,133 E | 11/1992 | Thorne | 422/99 |
| 5,183,564 A | 2/1993 | Hong | 210/232 |
| 5,190,734 A | 3/1993 | Frushour | 422/242 |
| 5,205,845 A | 4/1993 | Sacks et al. | 55/197 |
| 5,224,658 A * | 7/1993 | Smith | 241/27 |
| 5,246,665 A | 9/1993 | Tyranski et al. | 422/64 |
| 5,282,543 A | 2/1994 | Picozza et al. | 220/255 |
| 5,288,465 A | 2/1994 | Margolis | 422/102 |
| 5,308,584 A | 5/1994 | Vauramo | 422/104 |
| 5,319,436 A | 6/1994 | Manns et al. | 356/246 |
| 5,324,483 A | 6/1994 | Cody et al. | 422/131 |
| 5,342,581 A | 8/1994 | Sanadi | 422/101 |
| 5,424,213 A | 6/1995 | Mougin | 436/63 |
| 5,457,527 A | 10/1995 | Manns et al. | 356/246 |
| 5,484,731 A | 1/1996 | Stevens | 435/305.3 |
| 5,514,343 A | 5/1996 | Verwohlt et al. | 422/104 |
| 5,525,300 A | 6/1996 | Danssaert et al. | 422/99 |
| 5,540,891 A | 7/1996 | Portmann et al. | 422/102 |
| 5,593,642 A | 1/1997 | Dewitt et al. | 422/131 |
| 5,604,130 A * | 2/1997 | Warner et al. | 435/286.7 |
| 5,710,381 A | 1/1998 | Atwood et al. | 73/864.91 |
| 5,716,584 A | 2/1998 | Baker et al. | 422/131 |
| 5,741,463 A * | 4/1998 | Sanadi | 422/101 |
| 5,746,982 A | 5/1998 | Saneii et al. | 422/134 |
| 5,792,430 A | 8/1998 | Hamper | 422/131 |
| 5,858,693 A * | 1/1999 | Cottingham | 435/8 |
| 5,882,601 A | 3/1999 | Kath et al. | 422/102 |
| 5,888,454 A | 3/1999 | Leistner et al. | 422/52 |
| 5,897,842 A | 4/1999 | Dunn et al. | 422/131 |
| 5,922,289 A | 7/1999 | Wong | 422/102 |
| 5,948,363 A | 9/1999 | Gaillard | 422/102 |
| 5,961,926 A | 10/1999 | Kolb et al. | 422/101 |
| 5,993,745 A | 11/1999 | Laska | 422/104 |
| 5,996,818 A | 12/1999 | Boje et al. | 211/74 |
| 6,045,755 A * | 4/2000 | Lebl et al. | 422/65 |
| 6,054,100 A | 4/2000 | Stanchfield et al. | 422/102 |
| 6,149,882 A * | 11/2000 | Guan et al. | 422/211 |
| 6,165,417 A * | 12/2000 | Swierkowski | 422/100 |
| 6,274,088 B1 * | 8/2001 | Burbaum et al. | 422/101 |
| 6,395,552 B1 * | 5/2002 | Borade et al. | 436/37 |
| 6,455,007 B1 * | 9/2002 | Mansky et al. | 422/101 |
| 6,602,714 B1 * | 8/2003 | Tagge et al. | 436/2 |

FOREIGN PATENT DOCUMENTS

| | | |
|---|---|---|
| JP | 58035220 A * | 3/1983 |
| WO | 98/36826 | 8/1998 |
| WO | 99/64158 | 12/1999 |
| WO | 01/14529 | 3/2000 |
| WO | 01/00315 | 1/2001 |
| WO | WO 200207873 A2 * | 1/2002 |

OTHER PUBLICATIONS

Choi, Kwangwook, "Combinatorial Methods for the Synthesis of Aluminophosphate Molecular Sieves," Angew. Chem. Int. Ed. 1999, 38, No. 19, pp. 2891-2894.

Product Brochure "Titan Specialist Micro Titer Plates", Radleys; www.radleys.co.uk.

* cited by examiner

PARALLEL REACTOR WITH KNIFE-EDGE SEAL

RELATED APPLICATION

The present application is a continuation-in-part of U.S. patent application Ser. No. 09/607,535, filed Jun. 29, 2000 now U.S. Pat. No. 6,869,799 which is a divisional of application Ser. No. 09/093,870, filed Jun. 9, 1998 now U.S. Pat. No. 6,149,882.

BACKGROUND OF THE INVENTION

The present invention relates generally to parallel reactors, and more particularly, to a parallel reactor having a knife-edge seal.

The discovery of new materials with novel chemical and physical properties often leads to the development of new and useful technologies. The discovery of new materials depends largely on the ability to synthesize and analyze new compounds. Scientists are thus, always searching for a more efficient, economical and systematic approach for the synthesis of novel materials. Combinatorial technologies are often used to accelerate the speed of research, maximize the opportunity for breakthroughs, and expand the amount of available information. Combinatorial chemistry involves synthesizing microscale quantities of a compound and then testing thousands of compounds quickly.

The use of combinatorial technologies allows high density libraries of very large numbers of materials to be created using parallel synthesis. High throughput screens are then used to test these materials for desired properties to identify potential optimized compounds. Combinatorial technologies may be used to optimize and validate many variations of a material, formulation, or microdevice. Variables such as temperature, pressure, atmosphere, and concentration can be quickly adjusted and tested in a single experiment.

Once a combinatorial library is created, hundreds, or even thousands of compounds must be screened. Existing analytical methods and devices which were originally designed to characterize a relatively small number of compounds are often not well suited to screen combinatorial libraries. For example, in tradition catalyst development, researchers synthesize relatively large amounts of a candidate compound. The compounds are then tested to determine whether they warrant further study. For example, initial testing may involve contacting a compound with one or more fluid phase reactants. If the compound produces some minimal level of reactant conversion to a desired product, the compound undergoes more thorough characterization in a later step.

Because synthesis consumes a large fraction of the development cycle in tradition catalyst studies, researchers have expended little effort to speed up the screening step. Thus, although test reactors have been steadily improved over the years, most were simply automated to reduce labor needed to operate them.

SUMMARY OF THE INVENTION

An apparatus for testing compositions is disclosed. The apparatus improves productivity in testing variations of compounds by permitting large numbers of compositions to be tested simultaneously (in "parallel"); in an efficient manner.

An apparatus of the present invention generally comprises a base having a plurality of reaction wells formed therein and a sealing device positioned over the reaction wells for individually sealing each of the reaction wells. One of the sealing device and the base has chamfered ridges extending generally around a periphery of each of said plurality of reaction wells. The other of the sealing device and the base has a contact surface formed of a material softer than the material of the chamfered ridges to create a knife-seal between the sealing device and the base when the sealing device and the base are forced into contact with one another.

The ridges may, for example, be machined into a base which is formed from steel and the sealing device formed from aluminum, tin, copper, or nickel. The ridges may also be formed by upper ends of reaction vessels which are inserted into the reaction wells. The sealing device may be a cover placed over the vessels or a separate sealing plate interposed between the base and cover.

The sealing device may also comprise a plurality of sealing caps for sealing each of the reaction wells. The chamfered ridge is formed in a lower end of the sealing cap and creates a seal with a gasket positioned on the base around a periphery of the reaction well.

In another aspect of the invention, a parallel batch reactor comprises a base having a plurality of openings extending at least partially therethrough and a plurality of vessels sized for being received in the openings. Each of the vessels has a closed lower end and an open upper end having a chamfered periphery edge. The reactor further includes a sealing device formed from a rigid material softer than a material of the vessels such that the chamfered edges deform the sealing device when the sealing device is forced into contact with the chamfered edges to seal each of the vessels.

The above is a brief description of some deficiencies in the prior art and advantages of the present invention. Other features, advantages, and embodiments of the invention will be apparent to those skilled in the art from the following description, drawings, and claims.

BRIEF DESCRIPTION OF THE DRAWINGS

Corresponding reference characters indicate corresponding parts throughout the several views of the drawings.

DETAILED DESCRIPTION OF THE INVENTION

The following description is presented to enable one of ordinary skill in the art to make and use the invention. Descriptions of specific embodiments and applications are provided only as examples and various modifications will be readily apparent to those skilled in the art. The general principles described herein may be applied to other embodiments and applications without departing from the scope of the invention. Thus, the present invention is not to be limited to 11 the embodiments shown, but is to be accorded the widest scope consistent with the principles and features described herein. For purpose of clarity, details relating to technical material that is known in the technical fields related to the invention have not been described in detail.

The present invention provides an apparatus for rapidly screening members of a combinatorial library. High throughput screening is achieved by contacting a group of library members with a test fluid. Screening may be simultaneous for two or more library members or carried out in a rapid serial manner. Changes in the test fluid resulting from contact with library members are used to identify members worthy of further study. In the following disclosure, the term "fluid" refers to any substance that will deform continuously under the action of a shear force, including both gases and liquids.

The apparatus may be used to perform parallel synthesis or screening of materials or other experimentation involving reactions of multiple components. For example, the apparatus may be utilized for reactions where one or more components is a gas such as hydrogenations, carbonilations, oxidations and polymerizations with gaseous monomers. The apparatus may also be used with homogeneous, chiral, or heterogeneous catalysts (i.e., catalysts that enable catalytic reactions to occur with the reactants and catalysts residing in different phases (e.g., solid/liquid, solid/gas, liquid/gas)), or polyolefin and butyl rubber polymerizations. For example, in such applications, a plurality of heterogeneous catalysts (or catalyst precursors) having different compositions can be incorporated into the apparatus such that the plurality of catalyst candidates are simultaneously contacted with a reactant-containing fluid. The catalyst materials may be bulk or supported catalyst materials.

The disclosed invention is not limited to screening catalysts, but can be used for rapid screening of many different types of materials. For example, the apparatus can be used to screen library members based on their ability to filter out or adsorb a specific gas species. Similarly, polymeric materials synthesized using combinatorial methods can be screened for thermal stability by measuring the concentration of gaseous decomposition products in a fluid in contact with heated library members.

It is to be understood that the applications described herein are merely examples of uses of the apparatus of the present invention and that the apparatus may be used for other applications without departing from the scope of the invention.

Figure 1:
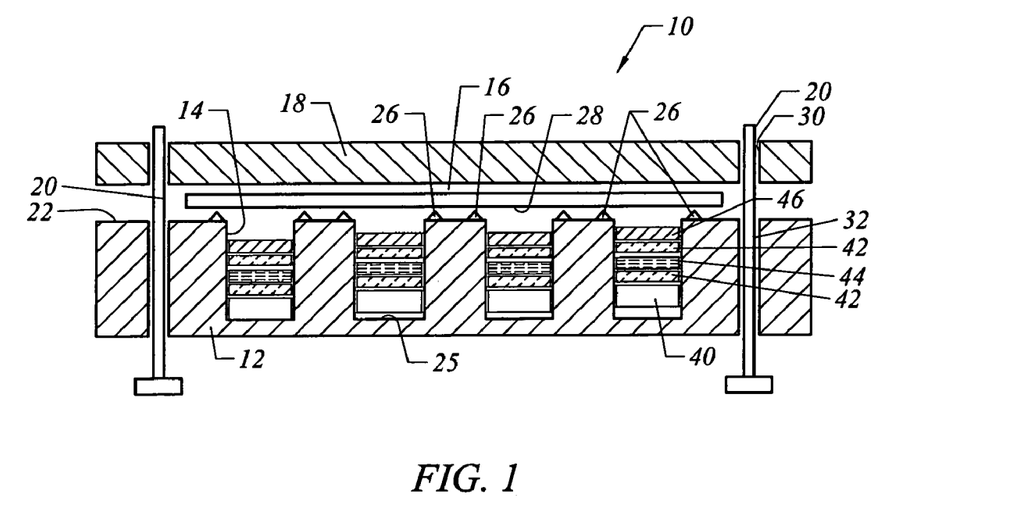
FIG. 1 is a schematic of a first embodiment of a parallel reactor of the present invention.

Referring now to the drawings, and first to FIG. 1, a parallel batch reactor is schematically shown and generally indicated at 10. The components of the apparatus 10 are shown spaced from one another in FIG. 1 to show details of the components. The reactor 10 includes a base member 12 having a plurality of reaction wells 14 formed therein and a sealing device (plate) 16 configured to create a seal with the base to individually seal the reaction wells. The reactor 10 further includes a cover member 18 and bolts 20 for attaching the cover to the base 12 and forcing the sealing device 16 into intimate contact with the base to create a seal. As further described below, an upper surface 22 of the base member 12 includes a plurality of chamfered ridges 26 which are used to create a knife-edge seal between the sealing device 16 and base. In order to create this knife-edge seal, the ridges 26 are formed from a material that is harder (e.g., has a higher Rockwell Hardness) than a material of the sealing plate 16. The knife-edge seal is created by the ridges 26 deforming a surface of the sealing device 16 at contact locations and in some instances the ridges may also cut into the sealing device.

Figure 2:
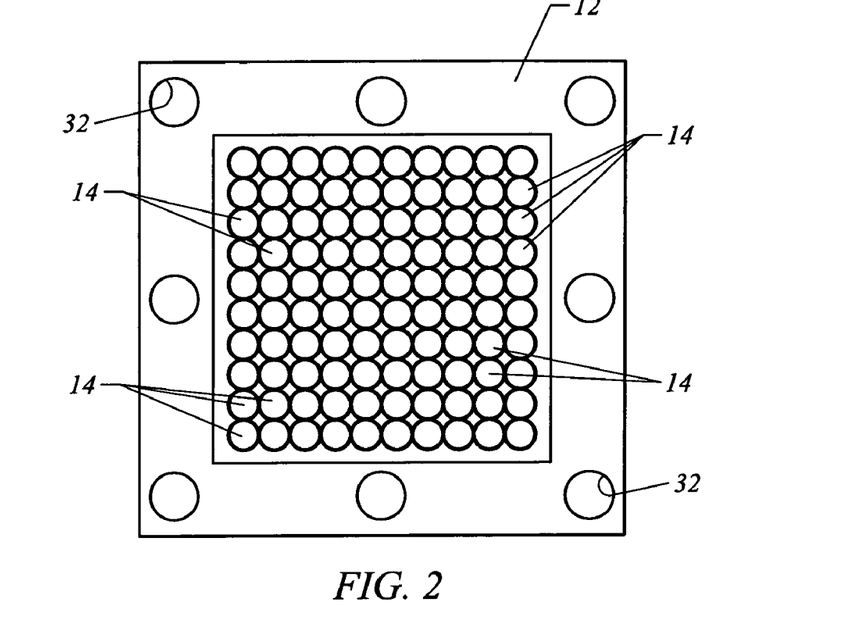
FIG. 2 is a plan view of a base of the reactor of FIG. 1.

The base member 12 may be formed from a material such as stainless steel or other relatively hard materials. The base 12 is preferably formed as a solid block with a plurality of openings extending partially therethrough to form the reaction wells 14. Components used in the synthesis or screening may be added directly to the reaction wells 14 or the reaction wells may be lined with an inert liner to prevent reactions between chemicals and the base member 12. As shown in FIGS. 1 and 2, the reaction wells are machined into an upper planar surface 22 of the base member 12 and are preferably machined as close as possible to one another.

The ridges 26 are preferably integrally formed with the base member 12 when the reaction wells 14 are machined into the base. The ridges 26 extend around a periphery of each of the reaction wells 14 to provide individual sealing for each reaction well. The chamfered ridges 26 preferably extend upwardly from the upper surface 22 of the base member 12 at an angle of approximately 45° to 90°. The ridges 26 may extend approximately 0.010–030 inch from the upper surface 22 of the base member 12, for example. The ridges 26 may also be formed separately from steel or other suitable material and attached onto the upper surface 22 of the base member 12. For example, the raised ridges may be formed as rings and placed around the periphery of each reaction well 14. The base 12 can then be formed from aluminum, titanium, Teflon, or nylon, for example, and can also be formed from a laminate construction. The chamfered ridges 26 may also be formed in the sealing device 16 rather than the base member 12, in which case the sealing plate 16 will be formed from a harder material than the base member. However, since the sealing plate 16 is easier to manufacture and replace than the base 12, the ridges are preferably formed on the base. If the ridges 26 are located on the sealing plate 16, the plate will have to be positioned such that the ridges are properly aligned with the reaction wells 14.

As shown in FIG. 2, the base member 12 includes 100 reaction wells 14 arranged in a rectangular array. The reaction wells may have an internal volume of between 10 and 500 μl, and more specifically an internal volume of approximately 120 μl, for example. It is to be understood that depending upon the scale of the apparatus, the base 12 may contain a greater or fewer number of reaction wells 14 of various geometric shapes arranged in any configuration. For example, the reaction wells 14 may be arranged to correspond to a standard microtiter plate format. The microtiter plate is a widely used means for handling, processing, and analyzing large numbers of small samples in the biochemistry and biotechnology fields. Typically, a microtiter plate contains 96 identical sample wells in an 8 by 12 rectangular array on 9 millimeter centers. A wide variety of equipment is available for automatic handling, processing, and analyzing samples in this microtiter plate format. The reactor may also be used in scaled up screening in which case the volume of the wells is larger and the number of wells smaller.

A bottom wall 25 of the reaction well 14 is preferably left with sufficient material to withstand pressures (e.g., 20 bar to 450 bar) applied to the bottom wall during reactions taking place within the wells. The base member 12 may also serve as a temperature control means for controlling the reaction temperature in the reaction wells 14, in which case the bottom wall 25 of the reaction wells is sized to provide the required conductivity between an external heat source, such as a heating plate on which the reactor 10 is placed, and the reaction wells. The reactor 10 may be placed on a temperature control plate which is contiguous to a lower surface of the base 12 for the transfer of thermal energy therebetween. The thermal control plate may be a plate formed of thermally conductive material with passages for conveying a heating or cooling fluid through the plate, or other heat generating device, as is well known by those skilled in the art. The reactor 10 may also be placed in an oven to heat the components within the reaction wells to 350°–400° C., for example.

The sealing plate 16 is formed from a relatively soft, rigid material such as aluminum, copper, tin, or nickel. As shown in FIG. 1, the plate 16 is sized to cover all of the reaction wells 14. The sealing plate 16 has a thickness sufficient to allow sealing with the chamfered ridges 26 of the base member 12 without initiating cracks in the plate. For example, the plate 16 may be between ⅛ and ¼ inch thick. The sealing plate 16 includes a generally smooth planer lower surface 28 for engagement with the ridges 26 of the base member 12. The sealing plate 16 is preferably replaced after each experiment.

The materials of the base member 12 and sealing plate 16 are preferably selected to be chemically suitable for the application (e.g., will not be attacked, solubilized, softened, or otherwise interact with the reagents, solvents, solids, products, or other components which are either added to the vessel or produced during a reaction sequence). The materials are also preferably chosen to assure that reactants, products, or by-products of the reaction are not adsorbed or otherwise trapped by the materials.

Figure 3:
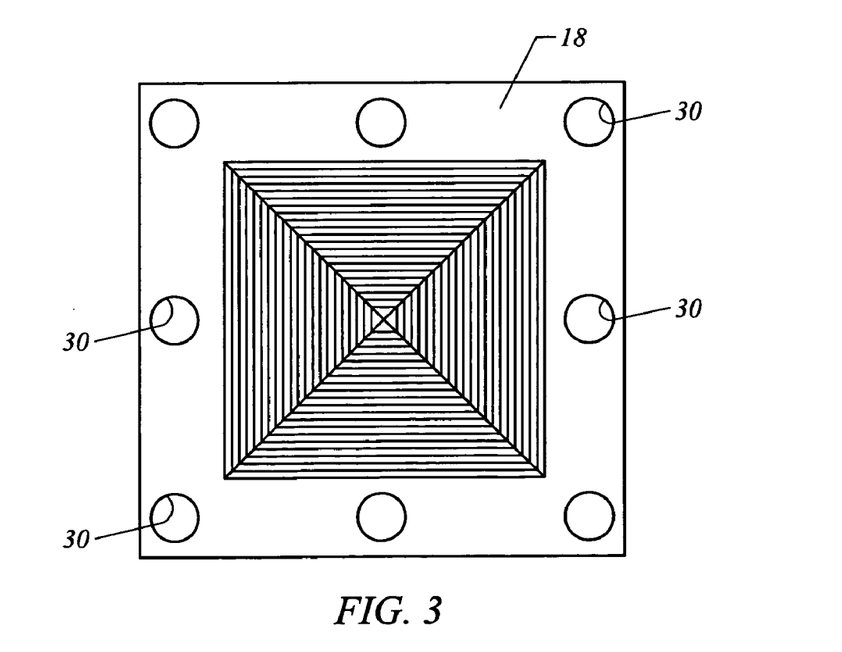
FIG. 3 is a bottom view of a cover of the reactor of FIG. 1.

The cover member 18 may be formed from the same material as the base member 12 or other material that is sufficiently rigid so that it does not deform when the bolts 20 are torqued. The cover 18 preferably has dimensions (length and width) generally corresponding to the dimensions of the base member 12 and includes openings 30 arranged to align with openings 32 in the base for receiving the bolts 20 or other suitable attachment means (FIGS. 1, 2 and 3).

The seal between the base member 12 and sealing plate 16 is created by applying a torque to the bolts 20 (e.g., 200 kg) which applies a force to the cover 18 which in turn forces the sealing plate into sealing engagement with the base 12. It is to be understood that attachment means other than bolts 20 may be used to force the sealing plate 16 into sealing engagement with the base 12. For example, external clamps (not shown) may be used to attach the cover 18 to the base 12.

The cover 18 may also be formed from a soft metal and the sealing plate removed so that a seal is created directly between the base member 12 and cover, as described below with respect to the second embodiment.

Figure 4:
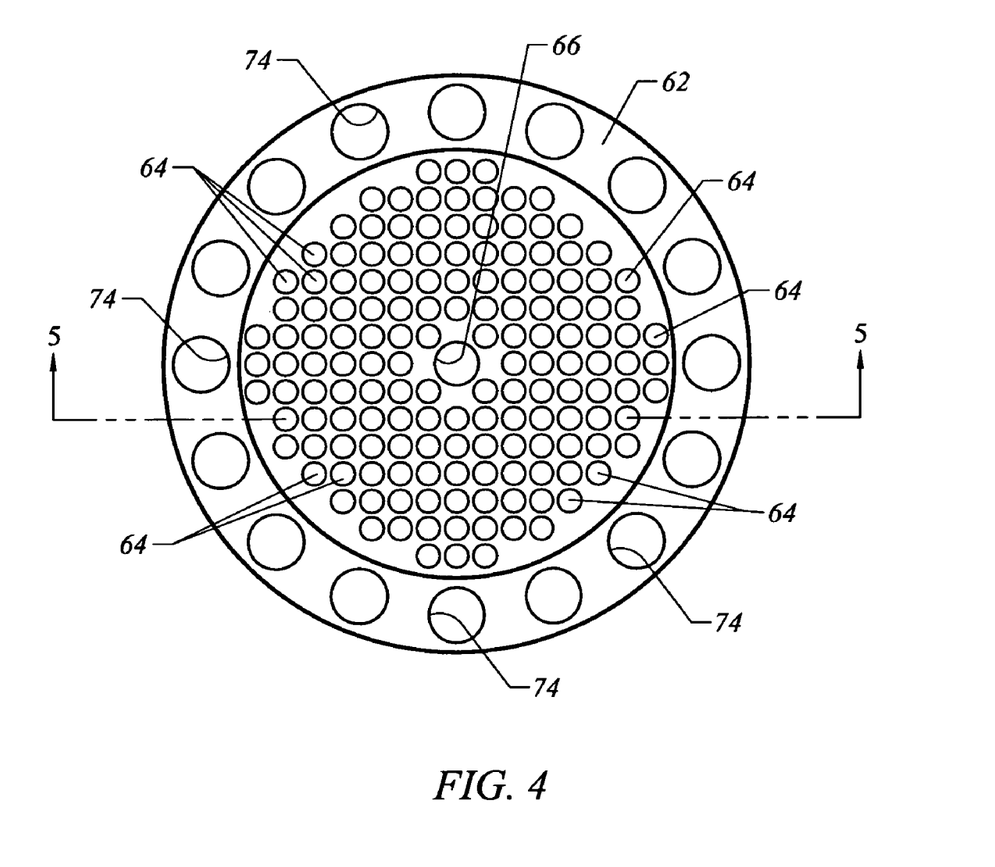
FIG. 4 is a plan view of a base of a second embodiment of the reactor of the present invention.
Figure 5:
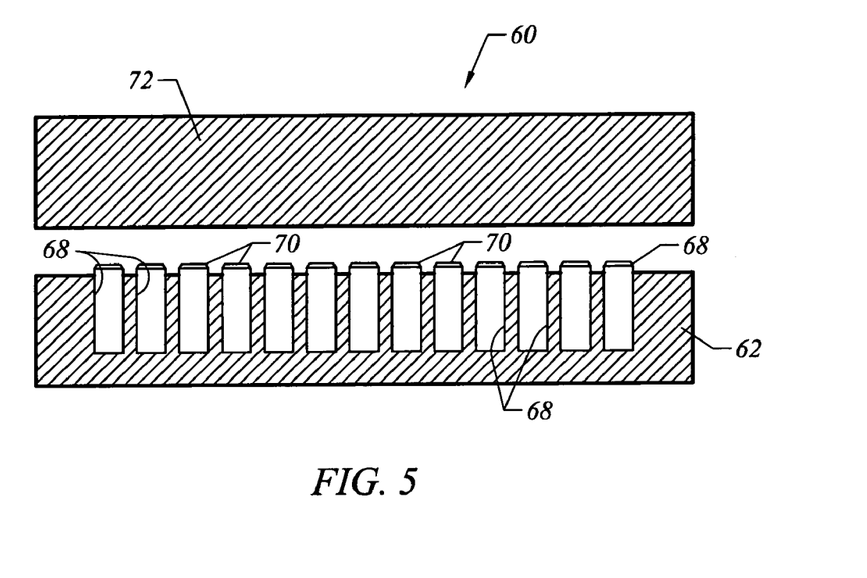
FIG. 5 is a cross-sectional view of the base of FIG. 4 and a cover taken in the plane including line 5—5 of FIG. 4.

FIG. 4 is a plan view of base member 62 of a second embodiment of the present invention, generally indicated at 60. The base member 62 is generally circular in shape and includes 152 reaction wells 64. A cross-sectional view of the base 62 taken in the plane including lines 5—5 of FIG. 4 is shown in FIG. 5 along with a cover 72. Reaction vessels (or vials) 68 are inserted into the reaction wells 64 for receiving components of the experiment. The vials 68 are formed from a hard material such as steel and the cover 72 is formed from a softer material such as aluminum, copper, tin, or nickel. Upper edges 70 of the vials 68 are chamfered to create a knife-edge seal when the edges of the vials are forced into the softer material of the cover plate 72. Bolts (not shown) are inserted into aligned openings 74 in the base 62 and cover 72 to force the cover into intimate contact with the vials 68. The base 62 and cover 72 may also include a central opening 66 for receiving a bolt or other attachment means.

A sealing plate as shown in FIG. 1 for the first embodiment, may also be interposed between the base 62 and cover 72 so that a seal is created between the sealing plate and base rather than the cover and base. Also, a coil spring (or elastomeric material) (not shown) may be placed at the bottom of the reaction wells 64 to force the vials 68 upward and bias the upper ends of the vials against the cover 72 or sealing plate.

Figure 6:
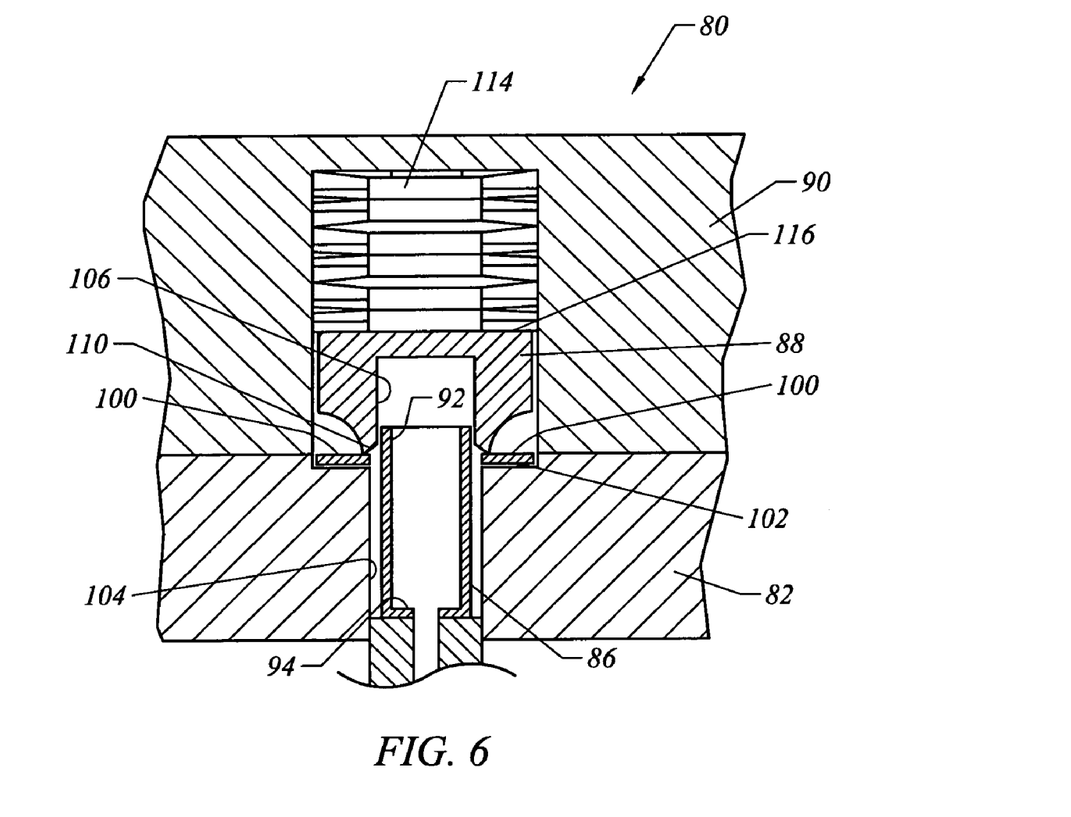
FIG. 6 is a cross-sectional partial view of a third embodiment of the reactor of the present invention.

FIG. 6 is a cross-sectional partial view of a parallel fixed bed reactor, generally indicated at 80. The parallel fixed bed reactor 80 may be, for example, a reactor as described in U.S. patent application Ser. No. 09/093,870, filed Jun. 9, 1998, which is incorporated herein by reference in its entirety. The reactor 80 includes a base member 82 configured to hold a plurality of vessels 86 (only one shown), a plurality of vessel covers (sealing caps) 88 configured to individually seal each of the vessels, and a cover member 90 for holding the vessel covers in place. The vessel 86 comprises a hollow right circular cylinder having a fluid permeable upper end 92 and lower end 94. A quartz paper frit (not shown) may be placed in the lower end 94 of the vessel 86 to hold a sample in place, but allow fluid to pass therethrough. A gasket 100 formed from a soft material such as copper, nickel, tin, or aluminum is seated in a groove 102 machined in the base 82 to form a contact surface of the base. The vessel cover 88 includes a cylindrical opening 106 for receiving the vessel 86. A lower end 110 of the vessel cover 88 is chamfered (e.g., forms a chamfered ridge) to create a knife-edge seal between the vessel cover and the gasket 100. Belleville washer springs 114 are placed above the vessel cover 88 within an opening in the cover member 90 to push against an upper surface 116 of the vessel cover and cause the lower end 110 of the vessel cover to deform or cut into the gasket 100, thereby forming a knife-edge seal. The gaskets 100 are preferably replaced after each experiment. The base 82 may also be formed from a soft material (e.g., aluminum, copper, tin, nickel) so that the vessel cover 88 can seal directly against the base 82 without the need for the gasket 100.

Use of the apparatus disclosed herein for combinatorial (i.e., high-throughput) approaches for screening libraries of materials may include an initial, primary screening, in which various materials are rapidly evaluated to provide preliminary data and optimally to identify several candidate materials having characteristics that meet or exceed certain predetermined metrics (e.g., performance characteristics, desirable properties, unexpected or unusual properties).

As shown in FIG. 1, a catalyst 40 may first be placed in the reaction well 14, followed by quartz paper 42 and ammonium carbonate (($NH_4$)$2CO_3$) 44 with another quartz paper 42 and barium oxide (BaO), sodium oxide ($Na_2O$), potassium oxide ($K_2O$), or strontium oxide (SrO) 46 for use in analyzing an aniline reaction. Each reactor well 14 may include, for example, 60 μl liquid reactant, 10 mg solid reagent, and 5 mg catalyst.

The following example illustrates principles and advantages of the invention.

An apparatus 10 having 100 reaction wells 14 as shown in FIG. 1 was used. Five milligrams of a catalyst was first placed in the bottom of each of the reaction wells 14. A quartz paper was placed over the catalyst and ten milligrams ($NH_4$)$2CO_3$ was put on the quartz paper. Sixty milligrams of BaO was placed over the second piece of quartz paper. The BaO was used to absorb $CO_2$ during the reaction. The sealing plate 16 was positioned over the reaction wells 14 and the cover 18 was aligned with the base 12. Bolts 20 were inserted into the aligned openings 30, 32 in the cover 18 and base 12 and torqued to force the sealing plate 16 into contact with chamfered ridges 26 of the base and seal each of the reaction wells 14. The reactor 10 was then placed in an oven at 300° C. for four hours.

The following reactions occurred:

$$(NH_4)_2CO_3 \rightarrow 2NH_3 + H_2O + CO_2$$

$$BaO + H_2O = Ba(OH)_2$$

$$BaO + CO_2 = BaCO_3$$

$$NH_3 + C_6H_6 + [O] \rightarrow Aniline + H_2O$$

Aniline yield up to 1% was reached in the reactor.

Although the present invention has been described in accordance with the embodiments shown, one of ordinary skill in the art will readily recognize that there could be variations made to the embodiment without departing from the scope of the present invention. Accordingly, it is intended that all matter contained in the above description and shown in the accompanying drawings shall be interpreted as illustrative and not in a limiting sense.

What is claimed is:

1. An apparatus for use in parallel reaction of materials, comprising:
   a base having a plurality of reaction wells formed therein; and
   a sealing device positioned over the reaction wells for individually sealing each of the reaction wells;
   one of the sealing device and the base having chamfered ridges extending generally around a periphery of each of said plurality of reaction wells, the other of the sealing device and the base having a metal contact surface formed from a material softer than a material of the chamfered ridges to create a knife-edge seal between the sealing device and the base when the sealing device and the base are forced into contact with one another.

2. The apparatus of claim 1 wherein the base and the sealing device are both formed from metal.

3. The apparatus of claim 1 wherein the base is formed from a material harder than the sealing device.

4. The apparatus of claim 3 wherein the base is formed from stainless steel.

5. The apparatus of claim 3 wherein the sealing device is formed from a material selected from the group consisting of aluminum, tin, copper, and nickel.

6. The apparatus of claim 1 further comprising a cover positioned over the sealing device.

7. The apparatus of claim 6 wherein the cover and the base each comprise a plurality of aligned openings for receiving bolts used to attach the cover to the base and force the sealing device into contact with the base.

8. The apparatus of claim 1 wherein the chamfered ridges are machined into the base.

9. The apparatus of claim 1 wherein said plurality of reaction wells comprises 100 or more reaction wells.

10. The apparatus of claim 1 wherein each of said plurality of reaction wells comprises a closed lower end and an open upper end for receiving components of the reaction.

11. The apparatus of claim 1 wherein each of said plurality of reaction wells has an internal volume of approximately 10 to 500 µl.

12. The apparatus of claim 1 wherein the base is generally rectangular in shape.

13. The apparatus of claim 1 wherein the base is generally circular in shape.

14. The apparatus of claim 1 wherein the sealing device is defined by a cover configured for attachment to the base.

15. The apparatus of claim 1 wherein the sealing device comprises a plurality of sealing caps for sealing each of said plurality of reaction wells and the chamfered ridges are formed in an end of the sealing caps and wherein the sealing device is formed from a material harder than the base.

16. The apparatus of claim 15 wherein the contact surface of the base comprises a plurality of gaskets each positioned around the periphery of one of said plurality of reaction wells.

17. The apparatus of claim 16 wherein the gasket is formed from a material softer than a material of the sealing caps.

18. The apparatus of claim 17 wherein the gasket is formed from copper and the sealing caps are formed from steel.

19. The apparatus of claim 15 wherein the sealing caps are spring biased against the base.

20. The apparatus of claim 15 further comprising a plurality of flow through vessels positioned within the reaction wells.

21. The apparatus of claim 1 wherein the apparatus is configured for use as a batch reactor.

22. The apparatus of claim 1 wherein the apparatus is configured for use as a fixed bed reactor.

* * * * *